April 28, 1959 R. E. SHEPHERD Plant Pat. 1,828
ROSE PLANTS
Filed Aug. 6, 1958
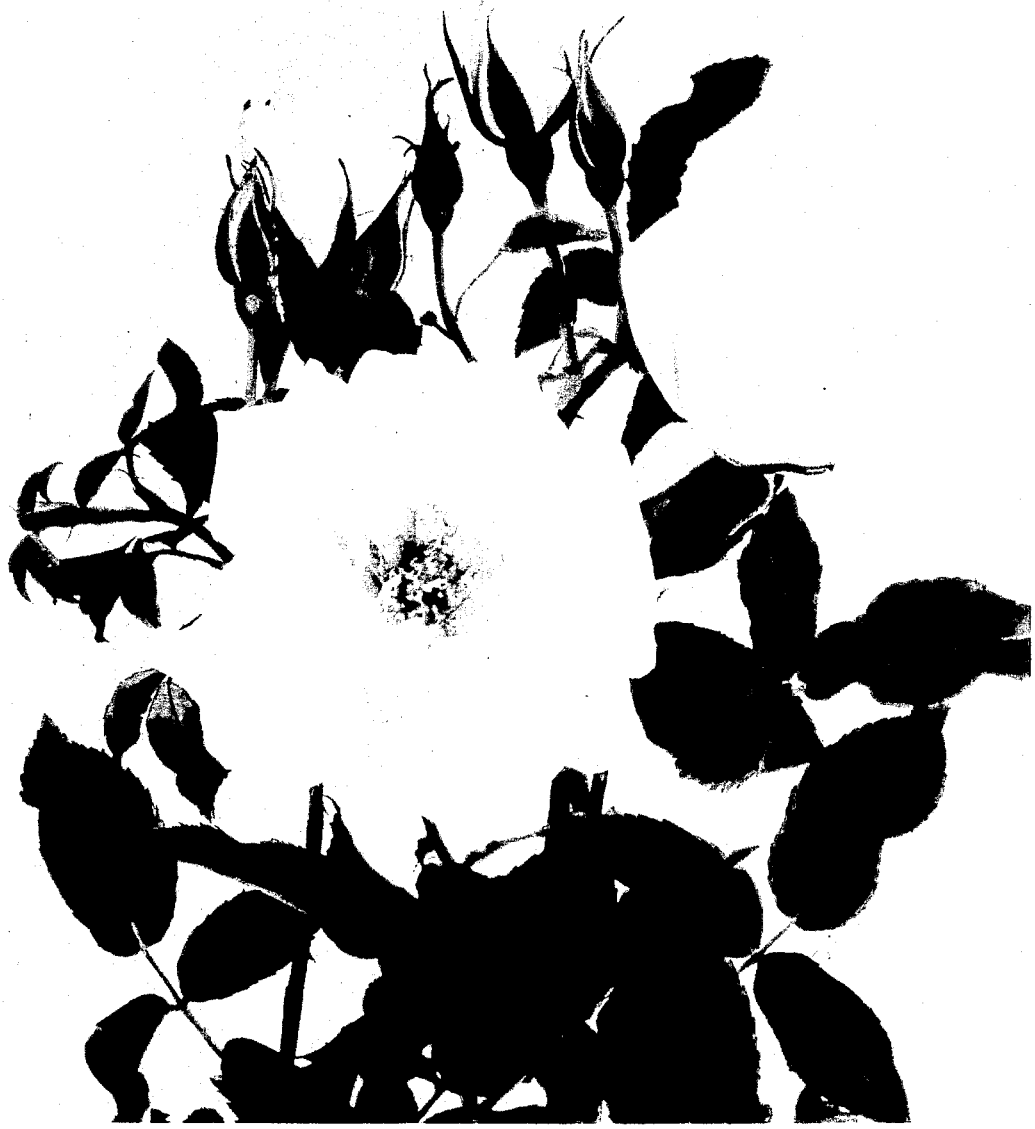
INVENTOR
Roy E. Shepherd
By Orville M Kile
Plant Pat. Agent United States Patent Office Plant Pat. 1,828
Patented Apr. 28, 1959

1,828

ROSE PLANTS

Roy E. Shepherd, Medina, Ohio, assignor to Edith C. Bosley, Mentor, Ohio

Application August 6, 1958, Serial No. 753,590

1 Claim. (Cl. 47—61)

My present invention relates to a new and distinct variety of floribunda rose plant which originated as a seedling resulting from breeding efforts made by me at my gardens near Medina. Its parentage is R. Dupontii (unpatented) × Pinocchio (Pl. Pat. No. 484) × Goldilocks (Pl. Pat. No. 672) × Feu Pernet-Ducher (Pl. Pat. No. 103). Its principal distinguishing features are the clear yellow color of its semi-double flowers and its healthy, dark-green foliage which is notably free from leafspot.

I have asexually reproduced this new variety in my gardens located near Medina, Ohio, by means of budding, and its distinguishing characteristics appear to be permanent.

The accompanying illustrations show several buds and blossoms of this new variety in various stages of opening, together with some of the stems and foliage.

In the following detailed description, color plate numbers refer to Ridgway's Color Standards and Nomenclature, whereas other color designations refer to the usual dictionary meaning.

*The plant*

Growth: Medium in height.
Form: Compact bush.
Blooming habit: Continuous and prolific bloomer.
Borne: Singly or in clusters of 2, 3 or 4.
Stems:
- *Color.*—Approximately Grass Green (Pl. VI).
- *Strength.*—Slender but strong and sturdy.
- *Type.*—Straight and upright, with rather short internodes.
- *Thorns.*—Sharp; slender; outward-pointing.

Foliage:
- *Quantity.*—Abundant, coming close to the flower.
- *Type.*—Pinnately compound, usually with 3 to 5 leaflets.
- *Size.*—Small to medium. Average terminal leaflet is approximately 2 inches long by 1 inch wide.
- *Shape.*—Slender ovate, with rounded base and pointed apex.
- *Color.*—Mature leaves are between Forest Green (Pl. XVLI) and Dusky Yellowish Green (Pl. XLI) on upper surface and Bice Green (Pl. XVII) on under surface, with edge approximately Garnet Brown (Pl. I). Young leaves are approximately Garnet Brown (Pl. I).
- *Aspect.*—Crinkled, glossy, and prominently serrated, with a notably dark-green, healthy appearance.
- *Rachis.*—Slender. Grooved above.
- *Stipules.*—Slender; clinging, except for sharp points.
- *Disease resistance.*—Compared with such varieties as Goldilocks (Pl. Pat. No. 672) and Mrs. Paul R. Bosley (Pl. Pat. No. 441) as grown under similar conditions, this new variety is much more resistant to blackspot.

*The flower*

Bud:
- *Color.*—When calyx first breaks, bud is Salmon Orange (Pl. II) to Scarlet Red (Pl. I), mostly the former. As the bud opens, these colors make stripes on the outer petals of the buds which are then predominantly bright yellow, the tone of which falls between Lemon Chrome (Pl. IV) and Empire Yellow (Pl. IV). Inner petals are deeper tones of the same color and, when looking into an opening bud, the inner petals appear to be much deeper in color because of the shadows.
- *Size.*—Just before calyx breaks, the bud is about ½ inch long; after breaking and before yellow shows in any quantity, the bud measures about 1 inch long; just before expanding, approximately 1¼ inches.
- *Shape.*—Conical to ovoid.
- *Sepals.*—Mostly simple, with some slight branching on some, and an occasional foliaceous extension.
- *Calyx.*—Pear-shaped; relatively large.
- *Peduncle.*—Not more than 2 inches in length. Slender but strong enough to hold bloom erect. Same color as stems.

Bloom:
- *Color.*—Half-open flower is between Pinard Yellow (Pl. IV) and Strontian Yellow (Pl. XVI), becoming slightly lighter in the fully opened flower. Sometimes the outer petals of a freshly opened flower is white, giving the effect of a white collar surrounding the yellow bloom.
- *Size.*—Fully opened flower averages approximately 2½ inches in diameter.
- *Form.*—Semi-double, with deep center surrounded by longer petals. When flower opens, the outer petals roll back slightly, making a flower which is almost straight across the top, finally opening rather flat revealing the pistils and stamens.
- *Longevity.*—Lasts moderately well both on bush and as cut flower.
- *Fragrance.*—Moderate.
- *Persistence.*—Petals cling until dried.
- *Petalage.*—Number of petals varies greatly in different specimens—from 25 to 45, including small inner petals and petaloids.

Petals:
- *Size.*—Outer petals are approximately 1¼ inches long and ¾ inch to 1 inch wide.
- *Shape.*—Obovate. Very slighly cupped. Edge prominently serrated.
- *Texture.*—Soft and silky.
- *Arrangement.*—Imbricated.

Reproductive organs:
- *Pistils.*—Many; tightly bunched. Styles—short. Stigmas—light yellow.
- *Stamens.*—Surround pistils. Filaments—irregular lengths but a little longer than styles. Anthers—orange-yellow, approximately Cadmium Yellow (Pl. III).

*Comparison*

The variety most like my new variety is Moonsprite (Pl. Pat. No. 1,450), but the two differ principally in that my new variety:

(1) Blooms earlier.
(2) Has more prolonged blooming season.
(3) Has bud that is more pointed.
(4) Color of flower is more gold, shading to white.

Having thus disclosed my invention, I claim:

The new and distinct variety of floribunda rose plant, characterized particularly by its vigorous, glossy, dark-green foliage with leaves crinkled and serrated; its great degree of blackspot resistance; and the clear golden yellow of its flowers, the outer petals of which sometimes shade to white in the open bloom.

No references cited.